United States Patent [19]

Tsao et al.

[11] Patent Number: 5,786,185
[45] Date of Patent: Jul. 28, 1998

[54] PROCESS FOR PRODUCING AND RECOVERING LACTIC ACID

[75] Inventors: George T. Tsao, West Lafayette, Ind.; Seo Ju Lee, Scotch Plains, N.J.; Gow-Jen Tsai, Monsey, N.Y.; Jin-Ho Seo, Seoul, Rep. of Korea; Donald W. McQuigg, Mooresville, Ind.; Susan L. Vorhies, Indianapolis, Ind.; Ganeshkumar Iyer, West Lafayette, Ind.

[73] Assignee: Reilly Industries, Inc., Indianapolis, Ind.

[21] Appl. No.: 480,881

[22] Filed: Jun. 7, 1995

Related U.S. Application Data

[63] Continuation of Ser. No. 279,902, Jul. 25, 1994, abandoned, which is a continuation of Ser. No. 954,444, Sep. 14, 1992, abandoned, which is a continuation-in-part of Ser. No. 759,896, Sep. 3, 1991, abandoned.

[51] Int. Cl.$^6$ ..................................................... C12P 7/56
[52] U.S. Cl. ........................... 435/139; 435/136; 210/660; 210/691
[58] Field of Search ............................. 435/139, 136; 560/185, 580; 562/584; 210/660, 691

[56] References Cited

U.S. PATENT DOCUMENTS

| | | | |
|---|---|---|---|
| 4,275,234 | 6/1981 | Banel et al. | 562/584 |
| 5,068,418 | 11/1991 | Kulprathipanja | 562/580 |
| 5,068,419 | 11/1991 | Kulprathipanja | 562/580 |

FOREIGN PATENT DOCUMENTS

| | | | |
|---|---|---|---|
| 0 135 728 A1 | 4/1985 | European Pat. Off. | 85/14 |
| 0 377 430 A1 | 7/1990 | European Pat. Off. | 90/28 |

OTHER PUBLICATIONS

Kawabata et al., *J. of Ferm & Bioeng.* vol. 68 No. 6, 1989, pp. 433–436.

R. Bajpai, E.L. Lanotti, C.J. Wang and B. Su, "Simultaneous Production and Recovery of Lactic Acid bu Fermentation", 1990 AICHE Spring Meeting.

Brian H. Davison and James E. Thompson, "Simlutaneous Fermentation and Separation of Lactic Acid in a Biparticle Fluidized Bed Bioreactor" May 6–10, 1991, Thirteenth Symposium on Biotechnology for Fuels and Chemicals.

*Primary Examiner*—Leon B. Lankford, Jr.
*Attorney, Agent, or Firm*—Woodard, Emhardt, Naughton, Moriarty & McNett

[57] ABSTRACT

Described is an improved fermentation process for producing lactic acid. The preferred process is conducted so as to form a fermentation broth containing undissociated lactic acid. The fermentation broth is contacted with an effective amount of solid-phase polymer containing pyridine groups to adsorb and increase rate of production of the free acid.

27 Claims, 5 Drawing Sheets

PROCESS FOR PRODUCING AND RECOVERING LACTIC ACID

REFERENCE TO RELATED APPLICATION

This application is a continuation of application Ser. No. 08/279,902, filed Jul. 25, 1994, now abandoned, which is a continuation of application Ser. No. 07/954,444, filed Sep. 14, 1992, now abandoned, which is a continuation-in-part of application Ser. No. 08/759,896, filed Sep. 3, 1991, now abandoned.

BACKGROUND OF THE INVENTION

The present invention relates generally to lactic acid production. More particularly, it relates to a novel fermentation process in which lactic acid is effectively produced in its undissociated ("free") form.

By way of further background, lactic acid has long been used in the food industry in the production of confectionary products, soft drinks, beers, wines, dairy products, baby foods, jams, salad dressings, etc. It is also used in the preparation of pharmaceuticals, cosmetics, agrichemicals and many other products. Recently, there has also been substantial academic and commercial interest in lactic acid as a potential raw material for producing biodegradable plastics. See, for instance, Lipinsky, E. S., and Sinclair, R. G., *Chem. Eng. Prog.*, Aug. 26, (1986).

Commercially, lactic acid is produced via both synthetic and fermentation processes. The synthetic process converts lactonitrile to lactic acid, with the lactonitrile starting material being available as a byproduct in acrylonitrile production. Van Ness, J. H., "Hydroxy Carboxylic Acids," in *Encyclopedia of Chemical Technology*, 3rd Ed., Wiley, Volume 13, pp. 80–103 (1981). On the other hand, in fermentation processes, bacteria or other microorganisms produce lactic acid as they metabolize carbon-containing (e.g. carbohydrate) raw materials. The growth and lactic acid-producing capacity of these organisms are inhibited by lactic acid itself and by low pH's. As such, measures have been taken in the past to minimize this inhibition. Most commonly, as it is formed, the lactic acid is immediately neutralized by an alkali such as NaOH, $NH_4OH$ or more commonly $CaCO_3$ thereby forming lactate salt and preventing pH drop and lactic acid buildup. Following the fermentation, the broth is acidified to convert the lactate salt to free lactic acid which is then separated from the broth. See, Buchta, K., "Lactic Acid", *Biotechnology*, H. Dellweg, Ed.), 3, 409 (1985). However, as has been recognized, this separation and purification is cumbersome and inefficient. Atkinson, B. and Mavituna, F., *Biochemical Engineering and Biotechnology Handbook*, the Nature Press, N.Y. (1983). Additionally, lactate itself inhibits lactic acid producing organisms, albeit to a lesser extent than lactic acid and low pH.

While several efforts have been made to increase lactate productivity by extracting it in situ, none to date has succeeded. Lactate has proven difficult to effectively extract, with no solvent or adsorbent having yet been found which avoids significant harm to lactic bacteria. Attempts to use electrodialysis to remove lactate salts have provided some improvement to productivity, but product concentrations remained low. See, for example, M. R. Friedman et al., *Biotechnol. Bioeng.*, 12, 961 (1961). Further, dialysis, not being specific for lactate, resulted in depletion of other medium components. Moreover, energy consumption by the electrodialyzer significantly impacts overall process economics.

In light of this background, there exists a continued need for a more effective and competitive microbial route to lactic acid. Such a microbial route would achieve high productivity and facilitate recovery of the final lactic acid product. The applicants' invention addresses these needs.

SUMMARY OF THE INVENTION

In brief summary, one preferred embodiment of the invention relates to an improvement in a fermentation process for producing lactic acid. The improved process includes the step of forming a fermentation broth containing free lactic acid. This lactic acid-rich broth is contacted with an effective amount of solid-phase polymer containing tertiary amine groups to adsorb and increase rate of production of the free acid.

By this preferred process, lactic acid has been produced at surprisingly high rates, typically expressed in grams per liter of working fermentation volume per hour ("g/L/hr"). Further, lactic acid is produced in undissociated or "free" form, as contrasted to other processes in which lactate salt (e.g. sodium or calcium lactate) is produced. As previously indicated, in these "lactate" fermentation processes, conversion of lactate salts to undissociated lactic acid is considered a predominant bottleneck and accomplished only at great complication and expense. Avoiding these and other problems, the applicants' invention thus provides important advantages on all scales, and especially when large scale lactic acid production is contemplated. These and additional objects and advantages of the invention will be apparent from the following description and appended claims.

DESCRIPTION OF THE PREFERRED EMBODIMENT

For the purposes of promoting an understanding of the principles of the invention, reference will now be made to certain embodiments and specific language will be used to describe them. It will nevertheless be understood that no limitation of the scope of the invention is thereby intended, such alterations, and further modifications and applications of the principles of the invention being contemplated as would normally occur to one skilled in the art to which the invention relates.

As indicated above, one preferred embodiment of the invention relates to a fermentation process for producing lactic acid. In this process, a carbon source is fermented to produce lactic acid. As is well known, such fermentations are conducted using bacteria, fungi or other microorganisms capable of forming lactic acid upon metabolizing a carbon source such as a carbohydrate. Typically, bacteria of the Family Lactobacillaceae are employed. As to Fungi, those of the Family Rhizopus can be employed, for example. It is well within the purview of one ordinarily skilled in this art to select and use a suitable lactic acid-producing bacterium or other organism from among the many known and available for this purpose. In the applicants' preferred work to date, *Lactobacillus delbrueckii* NRRL-B-445, and *Rhizopus oryzae* NRRL 395, obtained from the United States Department of Agriculture, Peoria, Ill., have been used.

The fermentation is conducted at a temperature suitable for the particular organism being used, typically between about 30° and 60° C. for bacterial fermentations. The applicants' preferred fermentations using *L. delbrueckii* have been conducted at about 42° C. For fungal fermentations, the fermentation temperatures may vary widely, but are often within the range of about 25° C. to about 50° C.

Likewise, the carbon source for the fermentation can be conventional. These include, for instance, carbohydrate-containing raw materials such as molasses, etc. Suitable solutions containing sugars such as glucose and sucrose can also be prepared and used without departing from the scope of the invention herein. Additionally, for fungal fermentations, raw materials such as barley, cassava, corn, oats and rice may be used as a carbon source. For further discussion of lactic acid fermentation processes, reference can be made to K. Buchta, "Lactic Acid", *Biotechnology*, H. Dellweg (Ed.) (1985), pp. 410–17.

As stated above, in prior known lactic acid fermentations, lactic acid which is formed is quickly neutralized to lactate salt to remove highly inhibitory lactic acid and maintain the fermentation pH at a level optimal for growth of the lactic acid-producing organism. This has been accomplished using basic substances, for instance sodium or ammonium hydroxide or calcium carbonate. In contrast, the applicants' preferred processes are conducted so as to form a fermentation broth that is rich in free lactic acid. This free lactic acid is then directly recovered as product as will be more particularly described below.

In preferred processes, the pH of the fermentation is initially controlled by the addition of a base such as sodium hydroxide. During this preliminary stage, the pH is preferably kept at or near the optimum growth pH for the fermentive microorganism employed. For instance, in Example 2 below, the pH was initially kept at about 5.5 to 6.0 in order to provide optimum growth conditions for *L. delbrueckii* and achieve a high cell density. Additionally, during this period an amount of lactate salt was formed which acted beneficially as a buffer during later stages of the fermentation.

Once a desired cell density had been achieved and buffering lactate salts were formed, the pH control of the fermentation was released. The fermentation pH then began to fall, and after it reached a level at which lactic acid production substantially decreased, the broth was contacted with the solid-phase polymer having tertiary amine groups to adsorb free lactic acid. Thus, the fermentive production of free lactic acid was coupled to its removal in situ by selective adsorption onto the the pyridine polymer. This adsorption of free lactic acid, in turn, decreases feedback inhibition in the system by the free acid and by pH's which would attend its buildup. Of course, an increased rate of lactic acid production accompanied the decrease in inhibition. This increased productivity can be observed for example by comparing the relative productivities (e.g. in g/L/hr) of analogous extractive and non-extractive fermentations. In highly advantageous extractive fermentations, productivities are increased at least about 50% over their non-extractive counterparts, and in more preferred work to date increases of up to about 100% or more have been demonstrated.

In fungal fermentations, it has been discovered that fungal growth occurs at the expense of lactic acid production. Thus, fermentive production of lactic acid employing Rhizopus is preferably conducted under non-growth conditions. That is, conditions of the fermentation are controlled so as to inhibit the growth of the fungus. This may be achieved, for instance, by using a fermentation medium that inhibits fungal growth. Such inhibition can be accomplished, for example, with a fermentation medium lacking a nitrogen source necessary for fungal growth, although other similar means may also be used.

When non-growth conditions are to be used during the major lactic acid production, the fungus is initially grown in the desired amount for the fermentation. During this growth period, of course, a medium fully supportive of growth is employed. Once the desired fungal growth has been achieved, the growth medium is removed and replaced with the growth-inhibiting fermentive medium. The fermentation is then conducted over a period of time, and, optionally, the growth-inhibiting medium can be temporarily replaced from time to time with a growth-supporting medium to rejuvinate the fungus.

The tertiary amine functions of the adsorbent polymer can be provided by N-heterocyclic or by N-aliphatic groups, preferably in their free base form. For example, AMBERLYST® A-21 resin, available from Rohm and Haas, Philadelphia, Pa., can be used in the invention. This A-21 resin contains aliphatic tertiary amine functions. For additional information about this and other similar resins, reference can be made to the literature including that available from the manufacturer. See, e.g., "AMBERLYST® A-21: technical bulletin fluid process chemicals," Rohm and Haas, April 1977.

In more preferred polymers, the tertiary amine functions are pyridine functions, for example as occur in polyvinylpyridine polymers. These polyvinylpyridine polymers have provided particular advantage in work to date, especially such polymers crosslinked with a suitable agent therefor, e.g. with divinylbenzene, and being either gel or macroreticular form resins. Further, crosslinking of at least about 2% has been preferred from work to date, although it can be greater for instance up to about 50% or more. A more preferred range, however, is about 2% to about 25% crosslinking.

To date, preferred polymers have been crosslinked poly (2- and 4-vinylpyridine) copolymers. Several of these copolymers are commercially available under the REILLEX™ family of trademarks from Reilly Industries, Inc. of Indianapolis, Ind. REILLEX™ 402 polymer, for example, has shown to be preferred, being a 2% cross-linked copolymer of 4-vinylpyridine and a commercially available divinylbenzene. REILLEX™ 402 polymer exhibits a convenient granular form having good thermal stability. Other preferred polymers have to date included, for example, a second cross-linked poly(4-vinylpyridine) copolymer commercially available under the REILLEX™ 425 trademark. This latter material is 25% crosslinked with divinylbenzene, and exhibits a convenient, highly porous macroreticular bead form also having good thermal stability. For more detail as to the chemical make-up and characteristics of these or other REILLEX™ polymers, reference can be made to relevant literature available either through the industry or from the manufacturer itself. One such reference is a brochure published by Reilly Industries, Inc. entitled *REILLEX™: A New Family of Cross-linked Polyvinylpyridines from Reilly (REILLEX™ Report 2,* 1986). It will be understood that in addition to these several REILLEX™ polymers, other solid polymers which contain pyridine groups to selectively adsorb the acid are also suitable for use in the applicants' invention. For instance, about 8 to 12% crosslinking is a desirable range and, as illustrated by Examples 4 and 5 below, an about 8% crosslinked gel-form poly 4-vinylpyridine resin has provided very high adsorptive capacities, and is thus particularly preferred thus far from this standpoint.

In preferred processes, the broth is separated from the fermenting medium and is filtered to remove cells (e.g. any fermentive microorganisms present) prior to contact with the polymer. The cells can then be returned to the fermentor, and the filtered broth passed through a column containing the polymer. It is preferred that such a column be kept at a relatively low temperature, e.g. between about 0° C. and about 30° C., more preferably about 15° C. to about 25° C., in order to keep the adsorptive capacity of the polymer relatively high. The free lactic acid is selectively removed from the broth as it passes through the column (i.e. the polymer substantially adsorbs free lactic acid as compared to lactate salt), and the eluent broth is returned to the fermentor. When the column has become relatively saturated with lactic acid, as can be determined for example by monitoring the influent and effluent pH of the broth, it can be replaced with another column containing fresh or regenerated polymer. This cycle can be repeated to provide a process which is highly productive and efficient for lactic acid. For example, in preferred processes lactic acid productivities ranging from about 1 up to about 4 g/L/hr have been achieved to date. Thus, by alternately contacting the broth with a plurality of (i.e. at least two) columns containing the polymer, the pH and lactic acid content of the fermenting medium can be maintained at acceptable levels for growth-related lactic acid production (e.g. pH above about 4 for the lactic acid bacteria) without addition of further neutralizing agents. Moreover, these fermentations have resulted in high cell densities and provided efficient conversion of the carbon source to the desired lactic acid product (e.g. about 60% or more of the carbon substrate converted to free lactic acid).

After the polymer is saturated, it is preferably water washed and the adsorbed lactic acid can be recovered using a suitable desorbing agent. Suitable desorbing agents will include for example polar organic solvents such as alcohols (e.g. methanol) as well as hot water. After elution from the column, the acid can be: isolated and worked up in a conventional manner. For instance, lactic acid can be concentrated by evaporation, distillation, or any other suitable means known in the art.

All references cited or referred to herein are hereby incorporated herein by reference as if fully set forth.

In order to promote a further understanding of the principles and advantages of the invention, the following Examples are provided. These specific Examples are intended to be illustrative and not restrictive of the invention, and it will be understood that all changes and modifications that come within the spirit of the invention are desired to be protected.

EXAMPLE 1

Extractive Fermentation Apparatus

Figure 1:
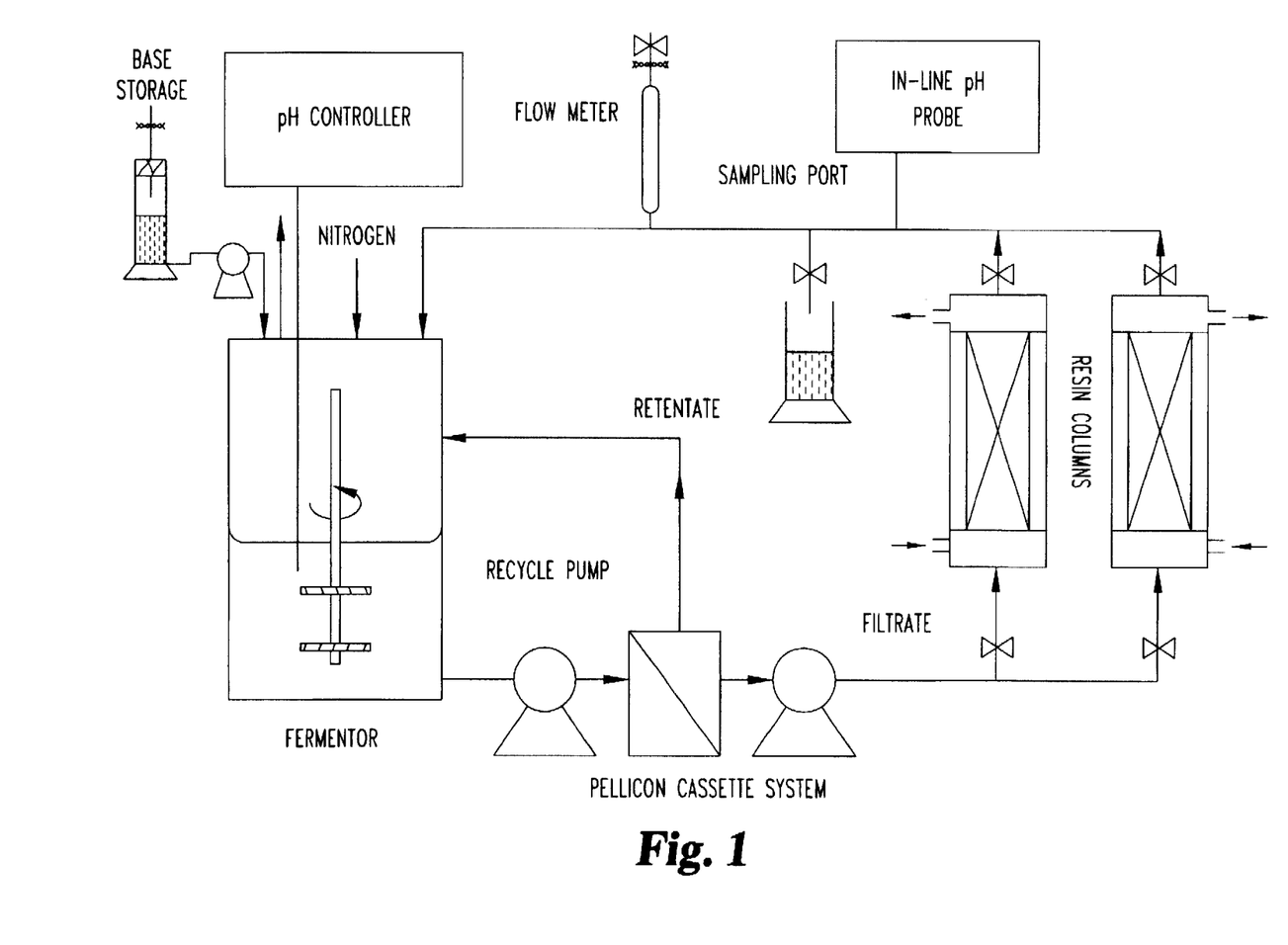
FIG. 1 is a diagrammatic representation of a fermentation apparatus used for preferred extractive fermentations of the invention.

The fermentation apparatus used for extractive fermentation processes described in Examples which follow is shown diagrammatically in FIG. 1. A fermentor having a capacity of 5 L working volume was equipped with a pH meter and a nitrogen sparge. The fermentor was connected to an acrylic PELLICON Cassette System (Model XX42 ASY60) available from Millipore Corporation of Bedford, Mass. Cell filtration was achieved with a PELLICON Cassette membrane (Millipore HVLP000C5) having a pore size of 0.45 μm and a filtration area of 0.46 m$^2$. This membrane is stable at pH's as low as 2. A Millipore XX8000000 variable speed pump circulated the fermentation broth from the fermentor and provided tangential flow across the membrane. The retentate from the cell filtration system was pumped back into the fermentor. The filtrate was circulated into one of two resin columns equipped with water jackets for cooling. Prior to use, each column was sterilized with methanol, and the methanol then eluted with sterile water. Each column measured 2.5 cm in diameter and was 60 cm long, and each was packed with 65 grams of Reillex™ 402 resin. The columns exited into a single line which circulated back into the fermentor. This line was equipped with in-line pH probe, a flow meter and a sampling port.

EXAMPLE 2

Extractive Fermentation Run

In the extractive fermentation apparatus described in Example 1, an extractive fermentation was conducted using *Lactobacillus delbrueckii* NRRL-B-445 obtained from the United States Department of Agriculture, Peoria, Ill. The organism was maintained at 4° C. on agar slants. The fermentation medium used was as follows, with anhydrous glucose (SIGMA) serving as a carbohydrate source and yeast extract (DIFCO) providing a nitrogen source:

| Glucose | 80 g/L |
| --- | --- |
| Yeast Extract | 48 g/L |
| Mineral salts: | |
| MgSO$_4$7H$_2$O | 1.34 g/L |
| FeSO$_4$7H$_2$O | 0.06 g/L |
| MnSO$_4$H$_2$O | 0.042 g/L |
| Sodium acetate | 1.23 g/L |
| K$_2$HPO$_4$3H$_2$O | 0.806 g/L |
| KH$_2$PO$_4$ | 0.062 g/L. |

The initial working volume was 1.1 L, and fermentation was carried out with nitrogen sparging and at a temperature of 42° C. Initially, the fermentation was allowed to proceed without circulating the broth out of the fermentor. During this initial stage, the fermentation and buildup of lactic acid was allowed to proceed for about 5 hours at which point the broth pH had reached about 5.5. Thereafter, the pH was maintained at 5.5 for approximately 6 hours by the automatic addition of 4.16N NaOH as necessary. 72 mL of NaOH were added over this 6 hour period, corresponding to the formation of 24.8 g/L of sodium lactate in the broth which acted effectively as a buffer in the system. A high cell density was also achieved. Following this initial buildup, the pH control was released by inactivating the NaOH pump. Over the next 4 hours, the pH of the broth dropped to about 4.3 and then the drop began to tail off. When the pH reached 4.22, the cell filtration system was activated, recycling the retentate back into the fermentor, and feeding the cell-free broth into one of the two resin columns (the other was shut off) at a rate of about 220 mL/hr. As the eluent from the column was recycled to the fermentor, the pH of the broth in the fermentor increased. This indicated that the resin was removing lactic acid faster than it was being formed in the fermentation broth. As the resin became loaded with lactic acid its absorptive capacity decreased, which was evidenced by a renewed downtrend in the pH beginning about 7 hours after the first resin column was brought online. After an additional 6 hours (about 31 hours into the fermentation process), the pH reached 4.25, whereupon the flow direction of the pumps was reversed to remove the broth entrapped in the resin from the first column. Then, the cell-free broth was directed instead into the second column and the pumps were reversed in order to return the flow to its initial direction. Again, the pH of the fermentation broth increased as a result of the resin removing lactic acid at a greater rate than its formation in the broth. This trend continued for about 7 hours, after which a downtrend was again observed as with the first resin column. After a total of 49 hours, the glucose was completely consumed and lactic acid formation ceased. At 52 hours, the extractive fermentation system was shut down.

Lactic acid was eluted from the resin columns by a slow feed of methanol. For the first column, entrapped glucose, lactate salt and lactic acid were first eluted before the eluted volume reached 115 mL. After that volume, lactic acid was eluted, reaching a maximum concentration of 48.4 g/L and totalling 11.4 g. For the second column, glucose was not eluted because the column was removed after glucose was completely consumed in the fermentation. The concentration of lactic acid for this column reached 64 g/L and totalled 13.3 g. These data correlate to a production of lactic acid at 0.98 g/L/hr. The in situ extraction significantly reduced the inhibition by free lactic acid, as well as prevented substantial and disruptive lowering of the broth pH which otherwise would have occurred.

Figure 2:
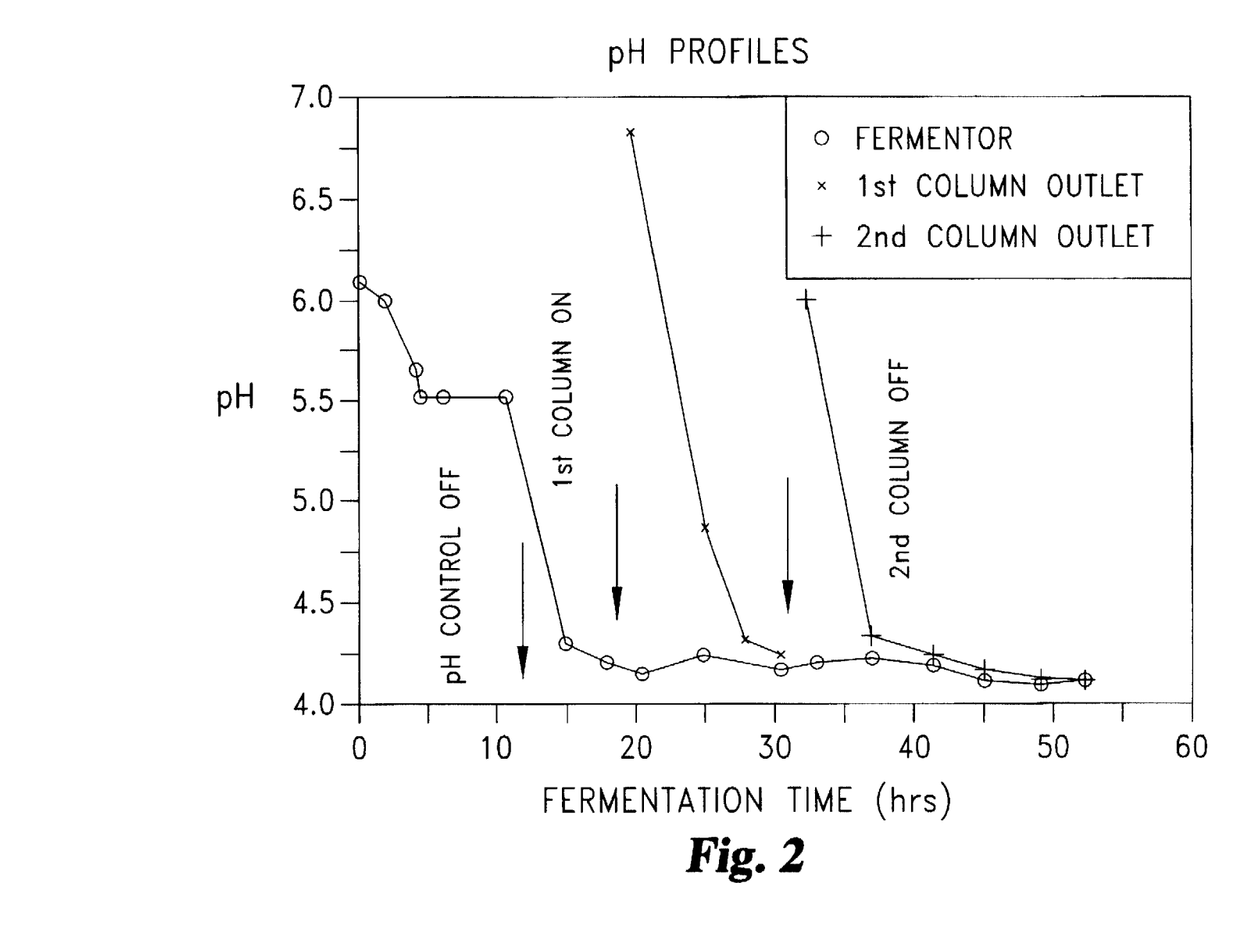
FIG. 2 is a graph of fermentation and effluent broth pH's versus time (hrs) for a preferred extractive fermentation.
Figure 3:
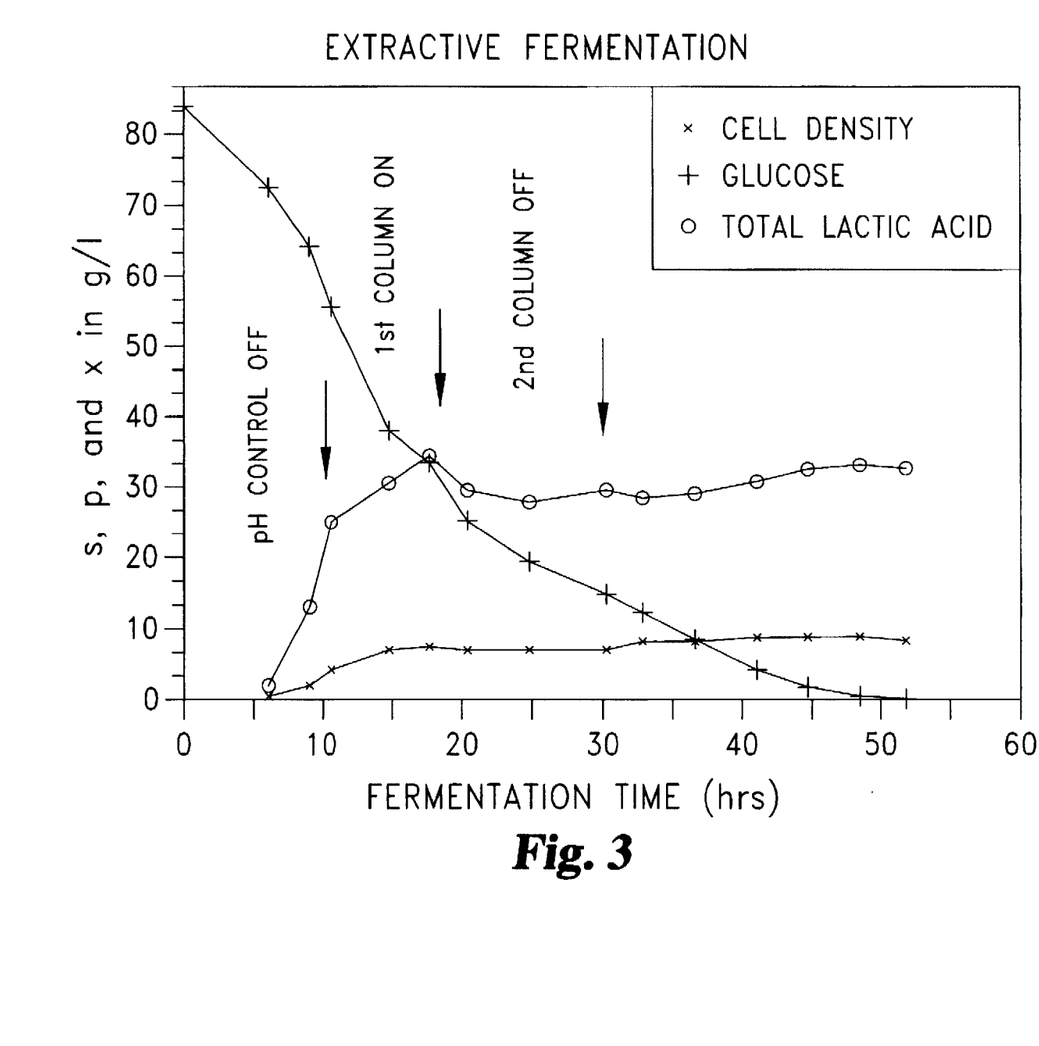
FIG. 3 is a graph of cell density, glucose concentration and total lactic acid concentration (free lactic acid+lactate) versus time for a preferred extractive fermentation.

Details of this entire operation are illustrated graphically in FIGS. 2 and 3. FIG. 2 is a graphical representation of the respective pH's of the fermenting medium and column effluent broth versus time (hrs). FIG. 3 is a graphical representation of the cell density and the glucose and total lactic acid concentration (free acid+lactate) in the fermentation medium as a function of time (hrs).

Two additional extractive fermentations were conducted analogous to that described above. In these additional runs, the amount of polymer vs. fermentation working volume was increased (about 242 g resin/L and 333 g resin/L, respectively), and productivities of 2.1 g/L/hr and 3.8 g/L/hr, respectively, were obtained. Excellent results are also obtained where the REILLEX™ 402 polymer is replaced with REILLEX™ 425 polymer.

EXAMPLE 3

Comparative Non-Extractive Fermentation

Figure 4:
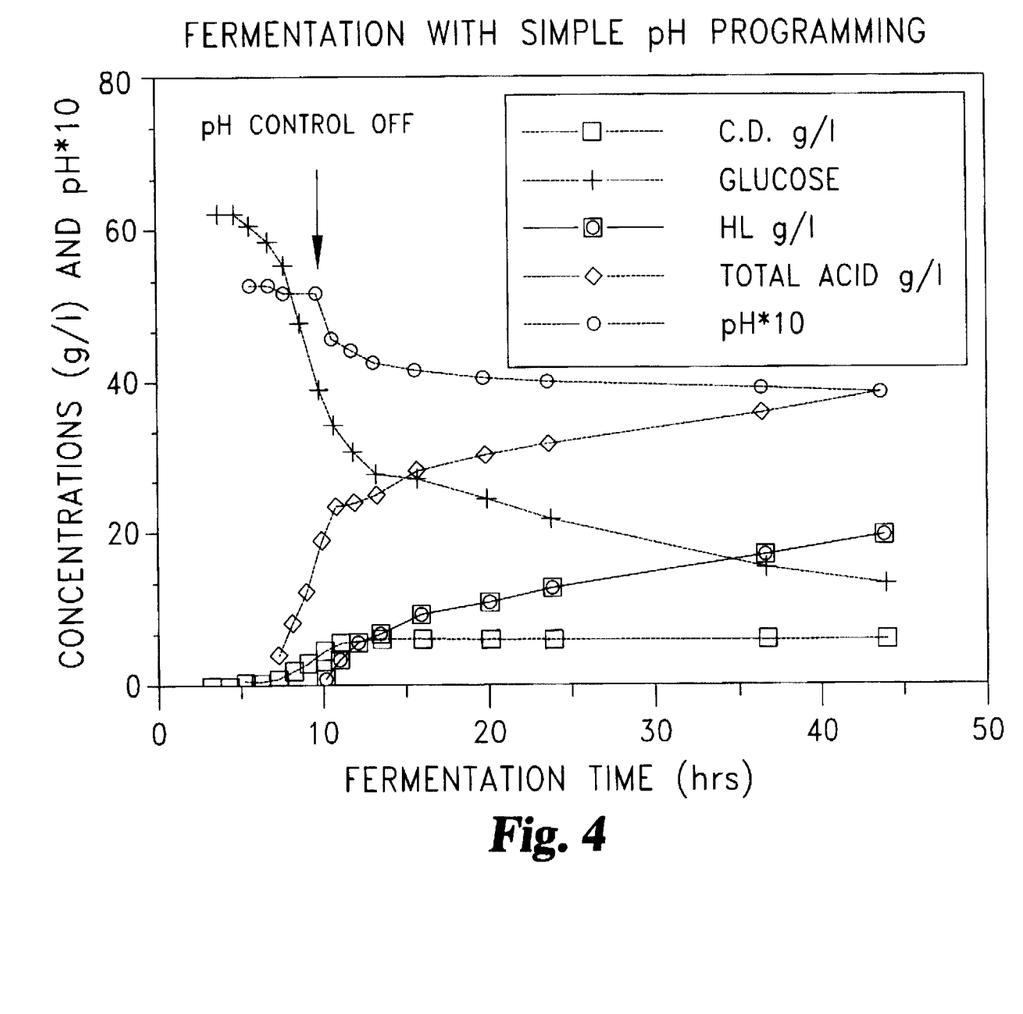
FIG. 4 is a graph of cell density, glucose concentration, free lactic acid concentration, total lactic acid concentration and fermentation pH×10 versus time for a comparative non-extractive fermentation.

The initial fermentation of Example 2 was repeated, only this time the fermentation was allowed to proceed in the fermentor without circulation of the broth through the resin columns. The results of this fermentation are shown in FIG. 4. As can be seen, the pH of the fermentation broth began to drop after the pH control was removed. The cell growth rate also declined, owing to the falling pH and inhibition by free lactic acid and/or other toxins produced in the fermentation. At the end of the fermentation, the lactate and free lactic acid ("Total Acid") totalled about 37 g/L, and the free lactic acid ("HL") totalled about 19 g/L. This free lactic acid was produced over approximately 35 hours, giving a production of free lactic acid of about 0.54 g/L/hr. It can thus be seen that the analogous extractive fermentation initially described in Example 2 provided an over 80% increase in lactic acid productivity.

EXAMPLE 4

Preparation of 8% Crosslinked Gel Poly-4-vinylpyridine

An aqueous solution was prepared by heating 300 mL of water to 40° C., adding 0.6 g of polyvinylalcohol (Airvol 205), and heating the slurry until it became clear. An organic phase was prepared containing 5 g of high purity divinylbenzene, 46 g of 4-vinylpyridine, and 0.5 g of Vazo 52. The aqueous solution was cooled to room temperature, added to a round-bottom flask, and stirred at a moderate rate under a nitrogen atmosphere. The organic phase was added to the stirred solution and the reaction mixture heated to about 50°–55° C. with continued stirring for 16 hours. After the reaction mixture was cooled, the gel beads were filtered, washed with water and then methanol, and dried overnight at room temperature.

EXAMPLE 5

Extractive Fermentation with 8% Crosslinked Material

Example 2 is repeated, except that an 8% crosslinked gel poly-4-vinylpyridine resin prepared as in Example 4 is used for the adsorption step. In this experiment, the 8% crosslinked material demonstrates superior adsorption capacity as a greater amount of lactic acid is adsorbed on the first column. This can remove the need for replacing the first resin column with a second fresh or regenerated resin column, or at least advantageously decreases the frequency at which this operation must be performed. As in Example 2, lactic acid can be eluted from the column with methanol.

EXAMPLE 6

Extractive Fermentation Using Amberlyst® A-21 Resin

Example 2 is again repeated, except using Amberlyst™ A-21 resin instead of the polyvinylpyridine resin. The lactic acid-loaded columns are rinsed with water, and lactic acid is desorbed with aqueous 5% $NH_3$ to give aqueous solutions of ammonium lactate. In other similar experiments, lactic acid can be removed from the A-21 resin by displacement on the resin with stronger acid, e.g. 5% aqueous sulfuric acid or hydrochloric acid. The stronger acid displaces the lactic acid with high efficacy while itself binding strongly to the resin. By monitoring the presence of the stronger acid in the effluent, a majority of the lactic acid can be recovered without any substantial contamination with sulfuric or hydrochloric acid.

EXAMPLE 7

Production of L+ Lactic Acid Using *Rhizopus oryzae*

In this example, the production of substantially pure L+ lactic acid was achieved by extractive fermentation according to the invention using the fungus Rhizopus oryzae. The L+ isomer of lactic acid is of increasing commercial importance as a source material for preparing biodegradable polymers.

Figure 5:
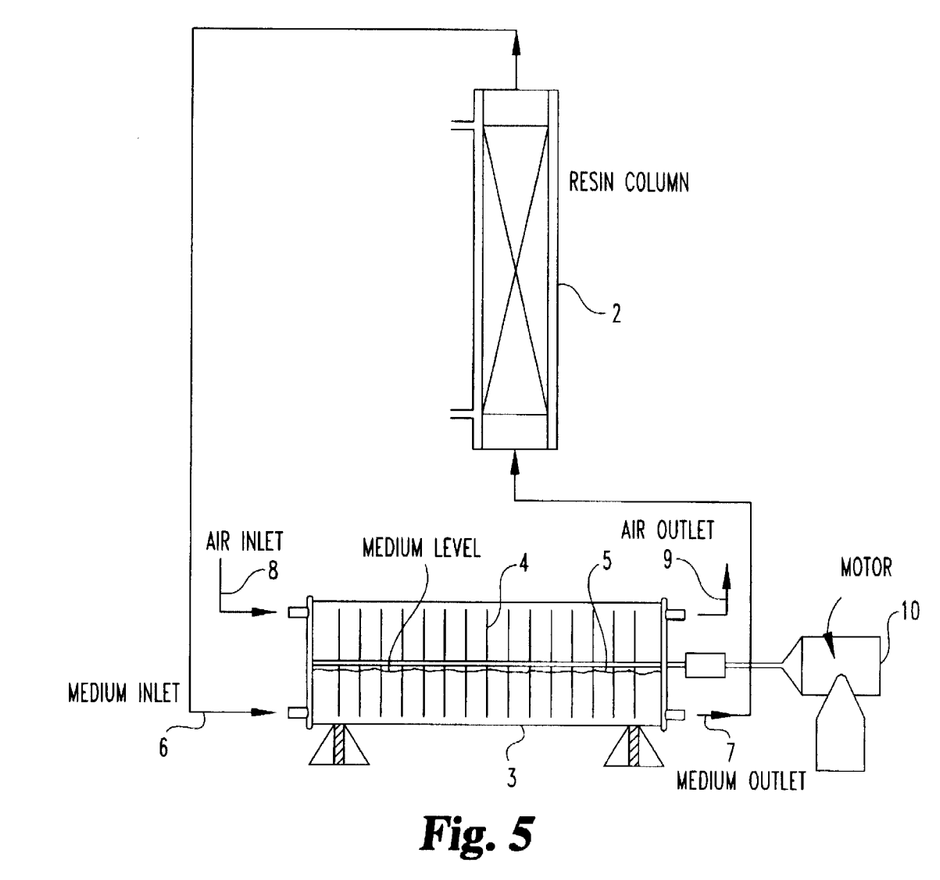
FIG. 5 is a diagram of the Rotating Biological Contactor (RBC) Apparatus used in Example 7.

Equipment:

The apparatus employed in this example is illustrated in FIG. 5. Generally, a Rotating Biological Contactor (RBC) 1 was coupled to a resin column 2 loaded with Reillex 425 polymer, available from Reilly Industries, Inc., Indianapolis, Ind. The RBC 1 generally comprises a fixed drum housing 3 in which a series of vertical disks 4 are mounted on a rotating horizontal shaft 5. The disks 4 are about half submerged when the RBC 1 is filled to the normal working level. The housing 3 has a medium inlet 6 and a medium outlet 7 positioned below the working level of the fermentation medium. The housing 3 also has an air inlet 8 and an air outlet 9. The rotating horizontal shaft 5 was driven by motor 10 at a speed of twenty-five revolutions per minute. For these experiments, the housing 3 was ~ten cm in diameter and ~thirty cm in length. The polypropylene disks 4 are ~nine and one-half cm in diameter.

Growth of Fungus

Approximately 1.25 L of growth medium was charged to the RBC 1. The growth medium contained glucose (100 g/l), urea (2.0 g/l), $MgSO_4*7H_2O$ (0.25 g/l), $KH_2PO_4$ (0.60 g/l) and $ZnSO_4*7H_2O$ (0.088 g/l). This growth medium was innoculated with a 20 ml innoculum of concentration $10^6$ spores/ml of *Rhizopus oryzae*, NRRL 395 obtained from the National Regional Research Laboratory, USDA in Peoria, Ill. The RBC 1 was thereafter operated at 25 rpm (without influx or outflux of the growth medium) to form a visible film of the fungus on the vertical disks 4. This growth period was conducted at room temperature (about 25° C.) while pumping air through the RBC above the working level of the fermentation medium at a rate of about 2 liters per minute.

Production of Lactic Acid:

After a visible film of fungus had been obtained, the RBC 1 was emptied of the growth medium and washed with sterile water. 1.2 L of a non-growth medium was then charged to the RBC 1. The non-growth medium comprised the following: glucose (100 g/l); $MgSO_4*7H_2O$ (0.25 g/l), $KH_2PO_4$ (0.60 g/l) and $FeCl_3$ (0.05 g/l). The RBC 1 was then operated at 25 rpm at room temperature while maintaining an air flow through the RBC of about 2 liters per minute. During operation, the fermentation medium was circulated from RBC 1 through resin column 2 via medium outlet 7 and medium inlet 6. Circulation of the fermentation medium was at a rate of about 2 liters per hour, and the medium was filtered as it exited medium outlet 7. The results of this run are set forth in Table 1.

TABLE 1

| Time (h)[a] | Medium pH[b] | Glucose in Medium |
|---|---|---|
| 0 | 3.69 | 83.62 |
| 5.25 | 4.38 | 69.2 |
| 23.22 | 4.40 | 65.00 |
| 43.50 | 4.49 | 60.00 |
| 69.00 | 4.50 | 60.00 |

[a]Measured from the beginning of medium circulation through the resin column.
[b]Measured at the RBC medium outlet.

This extractive fermentation provided the production of substantially L+lactic acid coupled to its removal from the fermenting medium to remove product inhibition. As can be seen, glucose consumption (and lactic acid production) continued for at least about a day. Additionally, only trace amounts of lactic acid were found in the medium over this period due to adsorption of the lactic acid on the resin column.

We claim:

1. A fermentation process for producing lactic acid, comprising:
   (a) providing a fermenting medium including a carbon source and a suspension of cells metabolizing said carbon source to produce free lactic acid;
   (b) continuously circulating and processing a fermentation broth away from and back to said fermenting medium, said continuously circulating and processing including the steps of:
      (i) separating the fermentation broth containing cells and free lactic acid from said fermenting medium;
      (ii) after said separating, filtering the cells from said fermentation broth;
      (iii) after said filtering, passing said fermentation broth containing free lactic acid through a column containing an amount of solid-phase polymer containing tertiary amine groups to adsorb the free lactic acid from the fermentation broth; and
      (iv) after said passing, returning said fermentation broth to said fermenting medium; and
   (c) wherein said continuously circulating and processing are effective to reduce feedback inhibition of the cells by the free lactic acid and maintain the pH of the fermenting medium above about 4, and to increase the production rate of free lactic acid by the cells in the fermenting medium.

2. A process according to claim 1, wherein said tertiary amine groups are pyridine groups.

3. A process according to claim 2, wherein said fermentation broth is formed using a lactic acid-producing bacterium, and also including the step of controlling the pH of the fermenting medium to increase cell density of the bacterium prior to said forming step.

4. A process according to claim 2, in which said contacting increases the lactic acid production rate by at least about 50%.

5. A process according to claim 4, in which lactic acid is produced at a rate of at least about 1 g/L/hr.

6. A process according to claim 5, in which said lactic-acid producing bacterium is of the family Lactobacillicae.

7. A process according to claim 6, in which said contacting further includes alternately passing said broth through at least two columns containing said polymer.

8. A process according to claim 7, and also including the step of adding base to the fermenting medium prior to said forming step to produce lactate salt buffer and to control pH to increase cell density of the bacterium.

9. A process according to claim 8, and including the step of adding base to the fermenting medium to produce lactate salt to replace lactate salt lost in said alternately passing step.

10. A process according to claim 7, in which the polymer is a polyvinylpyridine.

11. A process according to claim 10, in which the polymer is a poly 2- or 4-vinylpyridine.

12. A process according to claim 11, in which the poly 2- or 4-vinylpyridine is crosslinked with divinylbenzene.

13. A process according to claim 12, in which the poly 2- or 4-vinylpyridine is a macroreticular form resin.

14. A process according to claim 12, in which the poly 2- or 4-vinylpyridine is a gel form resin.

15. A process according to claim 12, in which the poly 2- or 4-vinylpyridine is at least about 2% crosslinked with divinylbenzene.

16. A process according to claim 15, in which said poly 2- or 4-vinylpyridine is about 2% to about 25% crosslinked with divinylbenzene.

17. A process according to claim 16, in which the polymer is poly 4-vinylpyridine crosslinked with about 2% divinylbenzene.

18. A process according to claim 16, in which the polymer is poly 4-vinylpyridine crosslinked with about 25% divinylbenzene.

19. A process according to claim 16, in which the polymer is a poly 4-vinylpyridine crosslinked with about 8% to about 12% divinylbenzene.

20. A process according to claim 19, in which the polymer is a gel form resin.

21. A process according to claim 1, in which the polymer is a polyvinylpyridine.

22. A process according to claim 1 wherein the fermentation is a bacterial fermentation.

23. A process according to claim 22 wherein the bacteria are of the Family Lactobacillaceae.

24. A process according to claim 23 wherein the bacteria are *Lactobacillus delbrueckii*.

25. A process according to claim 1 wherein the fermentation is a fungal fermentation.

26. A process according to claim 25 wherein the fungus is of the Family Rhizopus and produces substantially L+ lactic acid.

27. A process according to claim 26 wherein the fungus is *Rhizopus oryzae*.

* * * * *

UNITED STATES PATENT AND TRADEMARK OFFICE
CERTIFICATE OF CORRECTION

PATENT NO : 5,786,185
DATED : July 28, 1998
INVENTOR(S) : George T. Tsao et al.

It is certified that error appears in the above-identified patent and that said Letters Patent is hereby corrected as shown below:

In Section [63] of the cover sheet, the second line of said Section, please delete "954,444" and insert in lieu thereof —944,454—.

In col. 5, line 50, please delete the colon (":") after "be".

In col. 9, line 48 of Table 1, please delete "23.22" and insert in lieu thereof —23.00—.

Signed and Sealed this

Twenty-ninth Day of August, 2000

Attest:

Attesting Officer

Q. TODD DICKINSON

Director of Patents and Trademarks